United States Patent
Belle et al.

(10) Patent No.: US 8,007,836 B2
(45) Date of Patent: Aug. 30, 2011

(54) *CLEOME SPINOSA* EXTRACT USED IN PHARMACEUTICAL PREPARATIONS AND COSMETIC COMPOSITIONS

(75) Inventors: René Belle, Saix (FR); Françoise Belaubre, Villeneuve Tolosane (FR)

(73) Assignee: Pierre Fabre Dermo-Cosmetique, Boulogne-Billancourt (FR)

( * ) Notice: Subject to any disclaimer, the term of this patent is extended or adjusted under 35 U.S.C. 154(b) by 0 days.

(21) Appl. No.: 12/594,520

(22) PCT Filed: Apr. 4, 2008

(86) PCT No.: PCT/EP2008/054072
§ 371 (c)(1),
(2), (4) Date: Oct. 2, 2009

(87) PCT Pub. No.: WO2008/125520
PCT Pub. Date: Oct. 23, 2008

(65) Prior Publication Data
US 2010/0119632 A1 May 13, 2010

(30) Foreign Application Priority Data
Apr. 5, 2007 (FR) .................................. 07 54329

(51) Int. Cl.
*A61K 36/00* (2006.01)
*A61Q 7/02* (2006.01)

(52) U.S. Cl. ....................................................... 424/725

(58) Field of Classification Search .......................... None
See application file for complete search history.

(56) References Cited

U.S. PATENT DOCUMENTS
2004/0205910 A1 * 10/2004 Li et al. ............................. 8/406

FOREIGN PATENT DOCUMENTS

| FR | 2 853 245 | | 4/2003 |
|----|----|----|----|
| JP | 2001181129 A | * | 7/2001 |
| WO | WO2004-089390 | | 10/2004 |
| WO | WO 2004089390 A2 | * | 10/2004 |

OTHER PUBLICATIONS

Bulhoes et al, Phytochemical screening of plants native to northeastern Brazil. II, Anais da Faculdade de Farmacia, Universidade Federal de Pernambuco (1976), 15, 39-44.*
Database WPI Week 200166 Thomson Scientific, London, GB; AN 2001-586328 XP002456355 & JP2001181129 A, (2001), abstract.
De Albuquerque, "*Re-examining Hypotheses Concerning the Use and Knowledge of Medicinal Plants: A Study in the Caatinga Vegetation of NE Brazil*", J. Ethnobiology and Ethnomedicine, (2006) vol. 2, No. 30, pp. 1-10.
Buhl et al., "*Potassium Channel Conductance: A Mechanism Affecting Hair Growth both In Vitro and In Vivo,*" J. Investigative Dermatology, (1992) vol. 98, pp. 315-319.
Collins et al., "*New Cembranes from Cleome Spinosa,*" J. Nat. Prod. (2004) vol. 67, pp. 179-183.
Harmon et al., "*IL-1α Inhibits Human Hair Follicle Growth and Hair Fiber Production in Whole-Organ Cultures,*" Lymphokine and Cytokine Research, (1993) vol. 12, No. 4, pp. 197-203.
Jindo et al., "*The Effect of Various Cytokines on Hair Growth of Mouse Vibrissae in Organ Culture,*" (1994) 7 suppl, S73-S78.
Pagani et al., "*SUI Costituenti Dei Semi Di Cleome Pungens Willd,*" II Farmaco, (1967) vol. 22, p. 553.
International Search Report issued in application No. PCT/EP2008/054072 mailed on May 7, 2009.
French Preliminary Search Report issued in application No. 2 914 553 dated Oct. 26, 2007.

* cited by examiner

*Primary Examiner* — Qiuwen Mi
(74) *Attorney, Agent, or Firm* — Birch, Stewart, Kolasch & Birch, LLP.

(57) ABSTRACT

The invention relates to a *Cleome spinosa* extract used as an active ingredient in a cosmetic or pharmaceutical composition for extending the growth of hair follicles.

8 Claims, No Drawings

CLEOME SPINOSA EXTRACT USED IN PHARMACEUTICAL PREPARATIONS AND COSMETIC COMPOSITIONS

The present invention relates to the general field of pharmaceutical or cosmetic preparations treating hair fall.

*Cleome spinosa* Jacq. which has the synonym of *Cleome hassleriana Chodi*, is a herbaceous plant of the family of Capparidaceae and originates from the south east of Brazil and Argentina. It is very widely grown as an ornamental plant and many cultivars embellish road medians and roundabouts of our cities during summer from the end of June to September.

It is also commonly called sometimes "spiderflower".

The name of the genus *Cleome* would etymologically originate from the Greek word kleos which means "glory".

The genus *Cleome* comprises yearly herbaceous plants, subshrubs, rarely creepers. They may be inermed or armed with spiny stipules, the stems and the leaves are often pubescent with glandular hairs, with a strong smell.

The leaves are alternate, digitated with 3-9 folioles on an elongated leaf stalk, or unifoliolated and then sessile.

The flowers, bisexual, are grouped in racemes or axillary solitaries. They are generally zygomorphous and consist of 4 free sepals, 4 spatulate petals, with a nectariferous disc. The stamens, 6 in number, are exerted.

The cylindrical fruit is a dehiscent siliqua with 2 valves being set apart from the replum (or false partition) in order to release many kidney-shaped, more or less spherical grains.

The genus comprises about 80 neotropical species including 19 in Venezuela.

The species *Cleome spinosa* Jacq. differs from the other species by larger dimensions of its fructiferous organs: a gynophore from 20 up to 50 mm (versus 2-9 mm), large flowers with white or purple-tinted petals which are 10-25 mm long, purple stamens. The leaves include 5-7 folioles.

*Cleome spinosa* Jacq. is a glandulous, viscous, very spiny, yearly tall plant with a height of 1-2 meters. Flowers bloom in summer, with shorter petals than stamens. A gynophore separates the stamens of the disc. A linear tall fruit with a length of 6-12 cm.

The oil of the grains, rich in glucosinolates is used in empirical medicine against earaches and other diseases.

The aerial parts are not subject to use in traditional medicine. However, the plant is widely used as an ornamental plant.

*Cleome spinosa* has been the subject of very few scientific investigations both at a chemical and pharmacological level. Activity of *Cleome spinosa* as an inhibitor of collagenase was described as well as its use as "anti-ageing agent" (JP2001181129).

Dwight O. et al., worked on the phytochemical aspects of aerial parts of *Cleome spinosa* (Dwight et al., J. Nat. Prod. 2004, 67, 179-183). They thus describe in addition to a flavone, flindulatin, five novel cembranes belonging to the family of diterpenes, called cleospinol A, B, C, D and the 3'-hydroxy-isopentan-10-oate ester of cleospinol A.

The grains have already been the subject of a study describing the presence of glucosinolates, in particular glucocapparin [Pagini K. et al., Il Farmaco, Ed. Prat. 22, 553 (1967)].

Unexpectedly and surprisingly, the applicant demonstrated the use of an extract of *Cleome spinosa* as an active ingredient for preparing a pharmaceutical or cosmetic composition intended to extend growth of hair follicles.

The present invention first of all relates to the extract of *Cleome spinosa* which has an overall sulfur content between 0.05 g and 5 g for 100 g of dry material of the extract.

According to a feature of the invention, said extract of *Cleome spinosa* contains sulfur-containing amino acids, in particular cystine and methionine.

According to another feature of the invention, said extract contains from 0.01 g to 1 g of cystine for 100 g of dry material of the extract.

According to another feature of the invention, said extract contains from 0.001 g to 0.1 g of methionine for 100 g of dry material of the extract.

The present invention also extends to topical or oral cosmetic compositions containing such a *Cleome spinosa* extract.

Hair comprises: the hair stem (essentially consisting of a sulfur-containing protein "keratin" and pigments "melanin" which determine its color); and the hair bulb (the actual root of the hair), surrounded by the "peribulbar" area where the blood vessels which transmit all the essential nutritive elements are found in particular.

Hair does not grow continuously but according to a hair growth cycle divided in 3 phases. The growth (anagen phase), regression (catagen phase) and rest (telogen phase) phases succeed one another. During this latter phase, the hair is gradually moved out by a new anagen hair from the same follicle. The native hair will cause the fall of the mature hair.

Hair fall—either diffuse or localized—, as a hair disorder, is characterized by the increase in the number of hairs in the "catagen" phase.

The applicant has shown that an extract of *Cleome spinosa* stimulates the lengthening of the hair stem.

Within the scope of the present invention, the *Cleome spinosa* extract maintains, prolongs the anagen phase of the cycle described earlier. During this growth phase, hair is formed and grows by division of the cells of the hair follicle. The follicle is then implanted in the hypodermal tissue.

The anagen phase is primordial for the lengthening of the pilary stem of the hair.

The composition according to the present invention intended for stimulating and extending the growth of hair follicles comprises an extract of *Cleome spinosa* as an active ingredient.

Within the scope of the present invention, by hair disorders is meant any modification affecting the structure or functioning of the hair follicle. More particularly, by hair disorders, is meant any biological perturbation causing occasional or prolonged loss of hair. Capillary disorders may be of an occasional or established origin.

Capillary disorders may have different causes of internal or external origin. By internal origin, is meant any perturbation affecting biological processes involved in growing and maintaining hair. For example, sebaceous deregulation, enzymatic amplification of 5-alpha-reductase (hormonal deregulation), inflammation, structural modifications of collagen, intervention of growth factors, of nerve factors or vascular factors and the genetic component will be mentioned.

By external origin is meant the incidence of local flora of the scalp, the action of chemicals (colorations, perms, chemotherapies), pollution or life hygiene.

All these disorders of internal or external origin targeting the scalp has the direct consequence of perturbing and modifying the hair cycle leading to different forms of alopecias. The term of alopecia summarizes the whole of the pathologies affecting the hair follicle and the growth cycle of the hair stem and having the consequence of occasional and reversible loss or definitive fall of all or part of the hair. Two types of most widespread alopecias, alopecia aerata and androgenic or chronic alopecia will be mentioned.

By "*Cleome spinosa* extract" is meant in the sense of the present invention a *Cleome spinosa* extract preferably containing a total sulfur content comprised between 0.05 g and 5 g for 100 g of dry material of the extract.

The *Cleome spinosa* extract is chemically characterized by its sulfur content which assumes the form of sulfur-containing amino acids such as cystine, methionine. Total sulfur assayed after mineralization and a plasma emission assay has contents which vary depending on the solvents and on the extraction conditions from 0.05 g to 5 g for 100 g of dry material of the extract. Cystine may be assayed by high performance liquid chromatography; its contents also vary depending on the extraction conditions from 0.01 g to 1 g for 100 g of dry material of the extract. The methionine contents are smaller; they vary depending on the extraction conditions from 0.001 go 0.1 g for 100 g of dry material.

Advantageously, the *Cleome spinosa* extract according to the present invention is obtained from the leaves, flowers, fruit, stems, roots of *Cleome spinosa*; and preferentially from the dry blossomed aerial parts.

The present invention relates to the use of such an extract as an active ingredient for preparing a pharmaceutical composition intended to extend growth of hair follicles.

Preferentially, the pharmaceutical or cosmetic composition according to the present invention comprises an amount of dry extract of *Cleome spinosa*, as an active ingredient, comprised between 5 mg and 1 g for 100 g of said composition.

Advantageously, said amount of dry extract of *Cleome spinosa* is comprised between 10 mg and 500 mg for 100 g of pharmaceutical or cosmetic composition. Even more advantageously, said amount of dry extract of *Cleome spinosa* is comprised between 20 mg and 100 mg for 100 g of composition.

In the sense of the present invention, the *Cleome spinosa* extract acts as an active ingredient for stimulating and extending growth of hair follicles.

The extract according to the present invention promotes development of the pilary stem, improves the supply of elements which enter the composition of the hair, promotes maintaining the hair very close to the subcutaneous tissue which characterizes the anagen phase.

The active growth phase (anagen phase) is improved, extended.

The composition according to the present invention may further contain other active substances well-known to one skilled in the art, for anti-hairfall treatment: in a non-limiting way, mention will be made of: a quinquina extract (FR 2 853 245), minoxidil or 2,4-diamino-6-piperidinopyrimidine-3-oxide, vitamins such as vitamins A, E, B5, B6, C, H, PP, trace elements such as zinc, copper, magnesium, silicon, etc., protein derivatives such as peptides, sulfur-containing amino acids (of the methionine, cystine, cysteine type or derivatives), essential oils or extracts of plant origin with lipophilicity or hydrophilicity, the list of which is not limiting, antifungal agents such as piroctonolamine, undecylenic derivatives, cyclopiroxolamine, or chemical synthesis molecules reputed for their specific action at androgenic receptors or on the synthesis or expression of 5-α-reductases.

Finally, said preparation may also contain pharmaceutically acceptable excipients adapted for administration via an oral route or via a topical route.

Said composition preferably appears in a topical or oral form; and still more preferentially in a topical form.

Advantageously, the topical form is selected from the group consisting of a shampoo, gel, lotion, foam, spray, cream. This composition may also appear in oral form, such as a capsule, tablet, gelatin capsule, powder for drinkable suspensions.

In a particular embodiment of the invention, the composition according to the present invention may be used as a food supplement or dietary composition for extending the growth of hair follicles.

Said *Cleome spinosa* according to the present invention may be obtained as follows:
  milling of the dried blossomed aerial parts (leaves and/or flowers and/or fruit and/or stems) of *Cleome spinosa*.
  at least one extraction with a solvent which may be water, a $C_1$-$C_4$ alcohol, a ketone (methylethyl ketone, dimethyl ketone, methylisobutyl ketone), an ester (ethyl acetate, isopropyl acetate) or a mixture in any miscible proportion of these solvents.

The extraction is carried out in a plant/solvent ratio comprised between about 1/1 and 1/20 and may be renewed 2-3 times. The extraction temperature may be equal to room temperature right up to the boiling temperature of the extraction solvent.

The duration of the extraction may vary from 30 minutes to 72 hours and may be accomplished statically as well as under stirring: solid/liquid separation by techniques known to one skilled in the art. This may be a filtration or centrifugation operation for example.

The obtained solution may be used as such if the solvent used is compatible with its use. It may also be more or less concentrated until a dry extract is obtained. The concentrated solution may also be used.

A discoloration treatment may be undertaken by adding to the extracted solution, either concentrated or not, an absorbent support such as active coal or an absorbent resin. During the drying step, a support may be added in mass proportions relatively to the extracted raw material which may vary from 1-50%. The support may be maltodextrin, a sugar such as lactose, or silica. During the concentration step, it is also possible to add a high boiling point solvent such as glycerin, propylene glycol, butylene glycol, hexylene glycol. The *Cleome spinosa* extract is then solubilized in this new solvent.

The following preparations and compositions are mentioned as illustrative and non-limiting examples.

EXAMPLES FOR PREPARING THE PLANT EXTRACT

Example 1

100 kg of dried and milled blossomed aerial parts of *Cleome spinosa* are extracted with 1,500 kg of 95% (v/v) alcohol with stirring and reflux for 1 hour. After cooling, the extracted solution is recovered by filtration.

To this solution, 15 kg of active coal are added and the solution is refluxed for 20 minutes. The coal is removed by filtration. A pale yellow limpid solution is thereby obtained.

This solution is concentrated and then dried. 10 kg of dry extract are obtained. Its total sulfur content is 0.5 g for 100 g of dry material, its cystine content is 0.1 g for 100 g of dry material and methionine content is 0.015 g for 100 g of dry material.

Example 2

10 kg of dried and milled blossomed aerial parts of *Cleome spinosa* are extracted with 70 kg of 30% (v/v) alcohol with reflux for 2 hours and stirring. Once the solution is collected after filtration, the drug is again extracted under the same conditions as previously with 70 kg of 30% (v/v) alcohol. The obtained solutions are gathered together. 120 kg of a dark yellow liquid extract are thereby obtained. The total sulfur content is 1 g for 100 g of dry material of the liquid extract, cystine content is 0.2 g for 100 g and methionine content is 0.02 g for 100 g.

Example 3

1 kg of dried and milled blossomed aerial parts of *Cleome spinosa* are extracted with 10 liters of water at 80° C. for 5 hours and under stirring. The solution obtained by filtration is concentrated up to 2 liters, liters of propylene glycol are then added and the solution is filtered. 4 liters of a pale brown liquid extract are thereby obtained. For 100 g of dry material of this extract, the total sulfur amount is 1 g, the amount of cystine is 0.2 g and the amount of methionine is 0.02 g.

Example of Cosmetic Composition

Example 4

Anti-hairfall Lotion

| Compound | Amount (/100 g) |
|---|---|
| *Cleome spinosa* dry extract | 20 mg to 100 mg |
| Quinquina extract | 3 g to 6 g |
| 96% ethyl alcohol | qs |
| Hexylene glycol | 2.5% |
| Vitamin PP | 1% |
| Vitamin H | 0.003% |
| Beta-glycyrrhetinic acid | 0.3% |
| Decamethylcyclopentasiloxane | qs |
| Purified water | qsp 100 g |

Pharmacological Evaluation

Study of the effect of a *Cleome spinosa* extract on the growth of cultivated human hair follicles.

Exploration of the impact of different factors on hair growth may be investigated both in vivo and in vitro. Establishing simplified culture models representative of all the aspects of the behavior of the hair follicle in vivo is an indispensable step for optimizing evaluations of anti-hairfall products.

The culture of isolated hair follicle was developed by Philpott et al., in 1990. Growth of follicles was demonstrated for 10 days.

Several teams subsequently used alternatives of this model by adding growth factors or other molecular entities involved in the control mechanisms of hair growth: Buhl Al et al., J. Invest. Dermatol., 1992, March, 98(3): 315-319; Harmon C S et al., Lyphokine Cytokine Res., 1993, August 12(4): 197-203; Philpott M P et al., J. Dermatol. Sci. 1994, July, 7 suppl.: 573-78.

The extract of *Cleome spinosa* obtained according to Example 1 was evaluated on the direct growth of entire hair follicles from human scalp ex vivo for 14 days of culture. Evaluation of minoxidil, a reference molecule, was conducted in parallel.

Hair follicles originate from the human scalp from plastic surgery departments of hospitals or clinics (two donors).

The skin is shaved and washed in 6 baths of antibiotics. The follicles in the anagen phase are recognizable because they are very vascularized, and then isolated from the skin under a binocular magnifier and cleared of fat.

They are then incubated at 37° C. in 24-well culture dishes in an adequate culture medium containing the products to be tested.

The growth of the stem of the hair follicle is measured with plotting paper under a binocular magnifier on days 0, 4, 5, 7, 9, 12 or 14.

The determination of the growth and activity percentages of the hydroalcoholic extract of *Cleome spinosa* was carried out after 4 or 5, 7 or 8, 12 and 14 days of treatment of the hair follicles as compared with control non-treated follicles.

Notation: $T_x$ is the time x after treatment $T_0$ is time 0 of the beginning of the treatment The growth percentage is equal to ($T_x$ measurement−$T_0$ measurement)/$T_0$ measurement×100

The activity of the treatment is calculated in the following way: [($T_x$ treated measurement−$T_0$ treated measurement)−($T_x$ control measurement−$T_0$ control measurement)]/($T_x$ control measurement−$T_0$ control measurement)×100

The results are summarized in the following table:

| | % of activity | | | |
|---|---|---|---|---|
| | D4/D5 | D8/D7 | D12 | D14 |
| Minoxidil | 55 | 41 | 21 | 17 |
| *Cleome spinosa* extract | | | | |
| 10 µg/mL | 40 | 25 | 38 | 48 |
| 1 µg/mL | 27 | 34 | 22 | 23 |
| 0.1 µg/mL | 65 | 31 | 31 | 32 |

Stimulation of the growth of cultivated human hair follicles is observed for all the tested concentrations of *Cleome spinosa* extract.

The invention claimed is:

1. A method of stimulating growth of hair follicles in a subject in need thereof, said method comprises applying to the hair follicles of the subject a composition containing an effective amount of a *Cleome spinosa* extract.

2. The method according to claim 1, characterized in that the extract contains from 0.01 g to 1 g of cystine for 100 g of dry material.

3. The method according to any of claims 1 and 2, characterized in that the extract contains from 0.001 g to 0.1 g of methionine for 100 g of dry material.

4. The method according to claim 1, characterized in that the extract is present in the composition in an amount of between 5 mg and 1 g for 100 g of said composition.

5. The method according to claim 1, characterized in that the extract is present in the composition in an amount of between 10 mg and 500 mg for 100 g of said composition.

6. The method according to claim 1, characterized in that the extract is present in the composition in an amount of between 20 mg and 100 mg for 100 g of said composition.

7. The method according to claim 1, characterized in that the composition further comprises one or more active ingredients selected from the group consisting of a quinquina extract, minoxidil, vitamins, trace elements, protein methionine, cystine or cysteine, essential oils or extracts of plant origin with lipophilicity or hydrophilicity, and antifungal agents.

8. The method according to claim 7, wherein said composition includes quinquina extract.

* * * * *